(12) United States Patent
Franz et al.

(10) Patent No.: US 8,236,783 B2
(45) Date of Patent: Aug. 7, 2012

(54) ROS-SENSITIVE IRON CHELATORS AND METHODS OF USING THE SAME

(75) Inventors: Katherine J. Franz, Durham, NC (US); Louise K. Charkoudian, Palo Alto, CA (US)

(73) Assignee: Duke University, Durham, NC (US)

( * ) Notice: Subject to any disclaimer, the term of this patent is extended or adjusted under 35 U.S.C. 154(b) by 606 days.

(21) Appl. No.: 12/375,477

(22) PCT Filed: Jun. 29, 2007

(86) PCT No.: PCT/US2007/015258
§ 371 (c)(1),
(2), (4) Date: Aug. 19, 2009

(87) PCT Pub. No.: WO2008/020920
PCT Pub. Date: Feb. 21, 2008

(65) Prior Publication Data
US 2010/0004204 A1    Jan. 7, 2010

Related U.S. Application Data

(60) Provisional application No. 60/822,385, filed on Aug. 15, 2006.

(51) Int. Cl.
*A61K 31/69* (2006.01)
*C07F 5/02* (2006.01)
(52) U.S. Cl. ........... 514/64; 546/13; 564/8; 549/213
(58) Field of Classification Search .......... 514/64; 546/13; 549/213; 564/8
See application file for complete search history.

(56) References Cited

U.S. PATENT DOCUMENTS

| | | | |
|---|---|---|---|
| 5,663,201 | A | 9/1997 | Lowther et al. |
| 6,197,967 | B1 | 3/2001 | Vollmueller et al. |
| 6,329,378 | B1 | 12/2001 | Mei et al. |
| 6,989,397 | B1 | 1/2006 | Richardson et al. |
| 2002/0038004 | A1 | 3/2002 | Stolowitz et al. |
| 2004/0142851 | A1* | 7/2004 | Bonnemains et al. ............ 514/2 |
| 2004/0176326 | A1 | 9/2004 | Liu |
| 2006/0063739 | A1 | 3/2006 | Sun et al. |

FOREIGN PATENT DOCUMENTS
EP   1 382 603 A1   1/2004

OTHER PUBLICATIONS

International Search Report and Written Opinion, PCT/US07/15258, mailed Dec. 5, 2007.
Chang MCY et al. A selective, cell-permeable optical probe for hydrogen peroxide in living cells. J. Am. Chem. Soc. 2004; 126(47): 15392-15393.
McCord JM. Iron, free radicals, and oxidative injury. American Society for Nutritional Sciences. J. Nutr. 2004; 134: 3171S-3172S, expanded abstract.
Richardson DR and Ponka P. Pyridoxal isonicotinoyl hydrazone and its analogs: potential orally effective iron-chelating agents for the treatment of iron overload disease. J. Lab. Clin. Med. Apr. 1998; 131(4): 306-315.
Lovejoy DB and Richardson DR. Novel "hybrid" iron chelators derived from aroylhydrazones and thiosemicarbazones demonstrate selective antiproliferative activity against tumor cells. Blood. Jul. 15, 2002; 100(2): 666-676.
Tam TF et al. Iron chelator research: past, present, and future. Current Medicinal Chemistry. 2003; 10(12): 983-995.
Zhang GS and Suo Z. A mild and convenient synthetic method for arylhydrazones of methyl benzoate. Synthetic Communications. 2004; 34(4): 673-678.
Kalinowski DS and Richardson DR. The evolution of iron chelators for the treatment of iron overload disease and cancer. Pharmacological Reviews. 2005; 57(4): 547-583.
Miller EW et al. Boronate-based fluorescent probes for imaging cellular hydrogen peroxide. J. Am. Chem. Soc. 2005; 127(47): 16652-16659.
Simunek T et al. SIH—a novel lipophilic iron chelator—protects H9c2 cardiomyoblasts from oxidative stress-induced mitochondrial injury and cell death. Journal of Molecular and Cellular Cardiology. 2005; 39: 345-354.
Charkoudian LK et al. A pro-chelator triggered by hydrogen peroxide inhibits iron-promoted hydroxyl radical formation. J. Am. Chem. Soc. Published online Sep. 1, 2006: 2 pp.

* cited by examiner

*Primary Examiner* — Charanjit Aulakh
(74) *Attorney, Agent, or Firm* — Myers Bigel Sibley & Sajovec, P.A.

(57) ABSTRACT

The present invention provides compounds of Formula (I): along with compositions containing the same and methods of use thereof in treating oxidative stress.

9 Claims, 3 Drawing Sheets

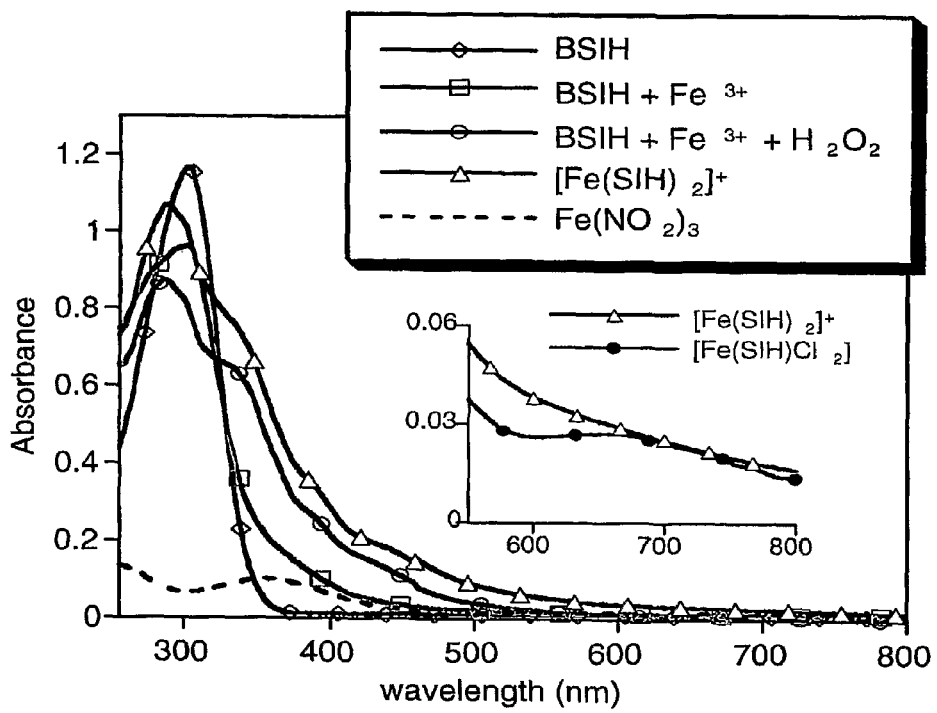
*Figure 1.* UV-vis spectra of 60 μM BSIH in MeOH in the absence and presence of 30 μM Fe(NO$_3$)$_3$, showing no complex formation.
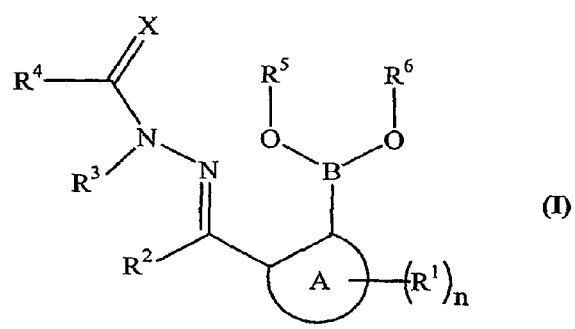
(I)

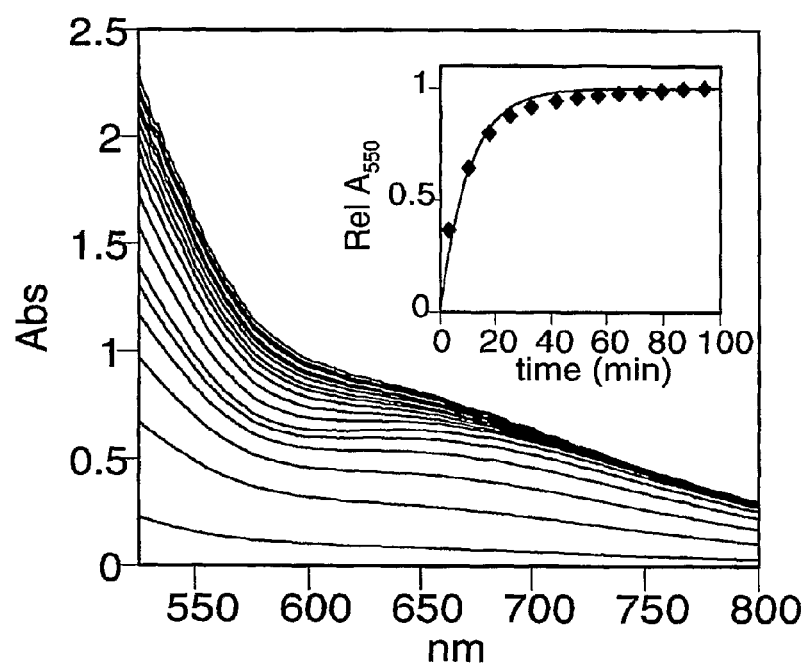
*Figure 2.* UV-vis spectra showing the formation of $[Fe(SIH)]^{2+}$ and $[Fe(SIH)_2]^+$ upon addition of $H_2O_2$ to a solution of $Fe(NO_3)_3$ and BSIH.

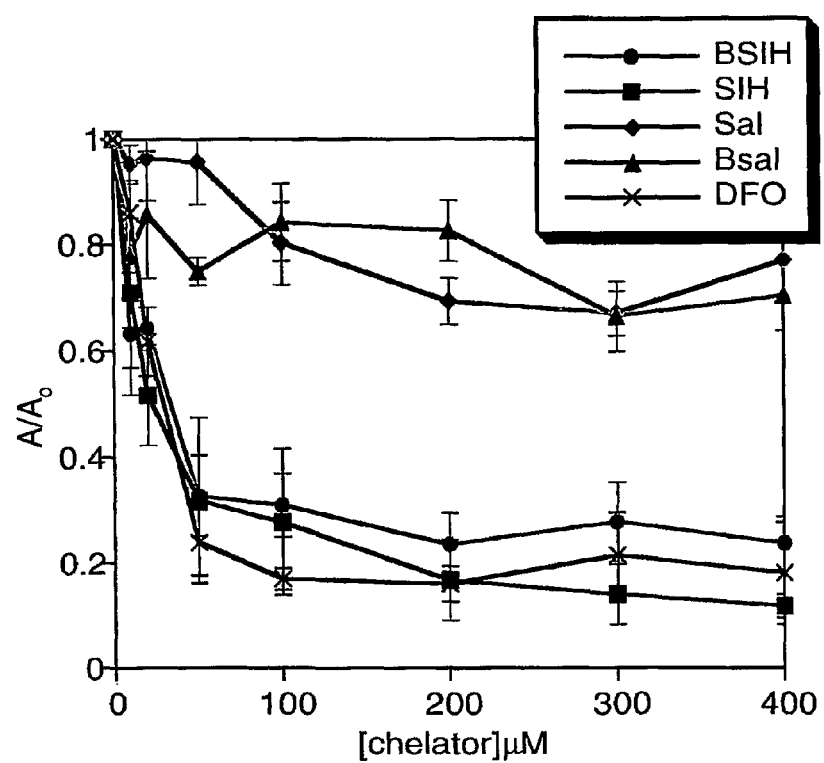
*Figure 3.* Effect of chelator concentration on deoxyribose degradation by OH.

ROS-SENSITIVE IRON CHELATORS AND METHODS OF USING THE SAME

RELATED APPLICATIONS

This application is a national phase application of PCT Application PCT/US2007/015258, filed Jun. 29, 2007, and published in English on Feb. 21, 2008, as International Publication No. WO 2008/020920, and which claims the benefit under 35 U.S.C. §119(e) of U.S. Provisional Patent Application Ser. No. 60/822,385, filed Aug. 15, 2006, the disclosure of each of which is incorporated herein by reference in its entirety.

FIELD OF THE INVENTION

The present invention concerns aroylhydrazone iron chelators, pharmaceutical formulations containing the same and methods of use thereof.

BACKGROUND OF THE INVENTION

Neurodegenerative diseases such as Parkinson's and Alzheimer's show signs of increased oxidative stress that result when reactive oxygen species (ROS) overwhelm a cell's inherent antioxidant mechanisms. Markers of oxidative stress include lipid peroxidation, DNA base hydroxylation, and protein modification, all of which are attributed to the highly reactive hydroxyl radical, OH.. While many potential antioxidant therapies use radical scavengers in attempts to mitigate cellular damage, such strategies do not inhibit formation of these harmful radicals (See Barnham, K. J et al., *Nat. Rev. Drug Disc.* 2004, 3, 205-214; Jellinger, K. A., *Drugs Aging* 1999, 14, 115-140; Shults, C. W., *Antioxid. Redox Signaling* 2005, 7, 694-700; Zecca, L. et al., *Nature Rev.* 2004, 5, 863-873).

A principal mechanism for the formation of OH. is via iron-promoted reactions like the Fenton reaction (Eq. 1) (Dunford, H. B., *Coord. Chem. Rev.* 2002, 233, 311-318), which becomes catalytic if cellular reductants can reduce $Fe^{3+}$ to $Fe^{2+}$.

$$Fe^{2+} + H_2O_2 \rightarrow Fe^{3+} + OH. + OH^-  \quad \text{Eq. 1}$$

In order for iron to promote Fenton chemistry, it must be in a coordination environment that favors redox cycling and allows reactants access to the inner sphere of the metal center (Liu, Z. D.; Hider, R. C., *Coord. Chem. Rev.* 2002, 232, 151-171). These requirements imply that loosely bound iron that is not properly regulated by the cell's normal metal trafficking and storage mechanisms contributes to oxidative stress. Chelating agents that can selectively sequester this pool of iron could potentially inhibit iron-promoted oxidative stress by inactivating the source itself. Although several chelators that were developed to treat iron overload diseases have some desirable properties for treating neurodegenerative diseases, they also have troubling drawbacks. Their high affinity for iron means that they compete with iron-binding proteins, thereby altering healthy iron distribution and inhibiting essential iron-containing enzymes. Furthermore, their intrinsic affinity for other metal ions disrupts the availability of key elements like zinc (Richardson, D. R., *Ann. NY. Acad. Sci.* 2004, 1012, 326-341; Youdim, M. B. H. et al., *Ann. NY. Acad. Sci.* 2004, 1012, 306-325; Kaur, D., et al., *Neuron* 2003, 37, 899-909; Ritchie, C. W., et al., *Arch. Neurol.* 2003, 60, 1685-1691; Benvenisti-Zarom, L. et al., *Neuropharmacol.* 2005, 49, 687-694).

SUMMARY OF THE INVENTION

To overcome these limitations, we here describe a class of pro-chelators that have little to no affinity for metal ions until a protective mask is selectively removed by ROS, as demonstrated in Scheme 1 for $H_2O_2$. In the absence of oxidative stress, these masked molecules are poor ligands that should not substantially alter healthy metal ion distribution, a common toxicity issue associated with currently available chelation therapies. Disease conditions that elevate oxidative stress, however, activate the chelator to reveal a high-affinity ligand that can scavenge and incapacitate redox-active iron that is the source of OH generation.

SCHEME 1

A first aspect of the present invention is a compound (sometimes also referred to as an "active compound") of Formula I:

(I)

wherein:
  X is O or S;
  A is aryl;
  n is an integer from 1 to 4;
  each $R^1$ is independently selected from the group consisting of: alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, arylalkyl, arylalkenyl, arylalkynyl, heteroaryl, heteroarylalkyl, heteroarylalkenyl, heteroarylalkynyl, alkoxy, halo, mercapto, azido, cyano, formyl, carboxylic acid, hydroxyl, nitro, acyl, aryloxy, alkylthio, amino, alkylamino, arylalkylamino, disubstituted amino, acylamino, acyloxy, ester, amide, sulfoxyl, sulfonyl, sulfonate, sulfonic acid, sulfonamide, urea, alkoxylacylamino, and aminoacyloxy;

$R^2$ and $R^3$ are each independently H, alkyl, or hydroxy;

$R^4$ is alkyl, cycloalkyl, heterocyclo, or aryl; and $R^5$ and $R^6$ are independently selected H, alkyl, or haloalkyl, or together form an alkylene bridge (optionally containing a fused aryl ring), which alkylene bridge may be unsubstituted or substituted from 1 to 4 times with alkyl, halo, and including pharmaceutically acceptable salts or prodrugs thereof.

A second aspect of the present invention is a pharmaceutical formulation (e.g. an oral dose formulation such as a tablet or capsule) comprising an active compound as described above in a pharmaceutically acceptable carrier.

A further aspect of the present invention is a method of treating a subject afflicted with an oxidative stress disease, comprising administering said subject a therapeutically effective amount of an active compound as described herein. The method may be used in a variety of applications, including but not limited to iron chelation therapy, subjects afflicted with a neurodegenerative disease such as Parkinson's disease, subjects afflicted with cardiovascular disease, subjects afflicted with cancer, subjects afflicted with age-related macular degeneration, subjects afflicted with iron overload disorder, subjects afflicted with hemochromatosis, subjects afflicted with β-thalassemia or Friedrich's ataxia, etc.

A still further aspect of the present invention is the use of an active agent as described above for the preparation of a medicament for the treatment of a disorder as described above.

The present invention is explained in greater detail in the drawings herein and the specification set forth below.

BRIEF DESCRIPTION OF THE DRAWINGS

FIG. 1. UV-vis spectra of 60 μM BSIH in MeOH in the absence and presence of 30 μM $Fe(NO_3)_3$, showing no complex formation. Addition of 0.6 mM $H_2O_2$ results in a spectrum (open circles) that matches that of $[Fe(SIH)_2]^+$ (triangles). The expanded view in the inset compares the mono and bis species $[Fe(SIH)Cl_2(CH_3OH)]$ and $[Fe(SIH)_2]NO_3$, respectively.

FIG. 2. UV-vis spectra showing the formation of $[Fe(SIH)]^{2+}$ and $[Fe(SIH)_2]^+$ upon addition of 100 mM $H_2O_2$ to a solution of 1.5 mM $Fe(NO_3)_3$ and 3.0 mM BSIH in MeOH.

FIG. 3. Effect of chelator concentration on deoxyribose degradation by OH.. A and $A_0$ are the absorbance at 532 nm in the presence or absence of chelator, respectively. Values below $A/A_o=1$ indicate protection of deoxyribose. Conditions: 200 μM $H_2O_2$, 10 μM $FeCl_3$, 2 mM ascorbic acid, 15 mM deoxyribose in pH 7.4 $NaHPO_4$ buffer.

DETAILED DESCRIPTION OF PREFERRED EMBODIMENTS

The term "treat" as used herein refers to any type of treatment that imparts a benefit to a patient afflicted with a disease or disorder, including improvement in the condition of the patient (e.g., in one or more symptoms), delay in the progression of the disease, etc.

"Oxidative stress disease" as used herein may be any disease that can be treated by the compounds and methods of the invention (and including disorders attributable to iron or copper induced oxidative stress) including but not limited to cancer, neurodegenerative disease, inflammatory disease, cardiovascular disease, diabetes, and iron chelation therapy subjects in general, etc.

"Iron chelation therapy" as used herein may be carried out on subjects in need of such treatment for any reason, including but not limited to subjects afflicted with cancer, neurodegenerative disease, cardiovascular disease, iron-overload disorders (e.g., from iron poisoning, hemochromatosis (iron overload disease), and transfusional hemosiderosis in Cooley's Anemia, sickle cell anemia, aplastic anemia and forms of leukemia), β-thalassemia, and Friedrich's ataxia. See, e.g., U.S. Pat. Nos. 6,989,397; 5,663,201; and 4,613,616.

"Cancer" as used herein may be any type of cancer, including but not limited to lung cancer, colon cancer, colorectal cancer, breast cancer, prostate cancer, ovarian cancer, liver cancer, leukemia, lymphoma, etc.

"Neurodegenerative disease" as used herein includes, but is not limited to, amyotrophic lateral sclerosis (or ALS), Parkinson's disease, Alzheimer's disease, multiple sclerosis, age-related macular degeneration, and expanded polyglutamine repeat diseases.

"Expanded polyglutamine repeat diseases" (or "polyglutamine repeat diseases") include, but are not limited to, Huntington's disease, dentatorubral pallidoluysian atrophy, spinobulbar muscular atrophy, and spinocerebellar ataxia types 1, 2, 3, 6 and 7. See, e.g. U.S. Pat. No. 6,632,616 to Burke et al.

"Pharmaceutically acceptable" as used herein means that the compound or composition is suitable for administration to a subject to achieve the treatments described herein, without unduly deleterious side effects in light of the severity of the disease and necessity of the treatment.

"Alkyl" as used herein alone or as part of another group, refers to a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, iso-pentyl, neopentyl, n-hexyl, 3-methylhexyl, 2,2-dimethylpentyl, 2,3-dimethylpentyl, n-heptyl, n-octyl, n-nonyl, n-decyl, and the like. "Lower alkyl" as used herein, is a subset of alkyl, in some embodiments preferred, and refers to a straight or branched chain hydrocarbon group containing from 1 to 4 carbon atoms. Representative examples of lower alkyl include, but are not limited to, methyl, ethyl, n-propyl, iso-propyl, n-butyl, iso-butyl, tert-butyl, and the like. The term "alkyl" or "loweralkyl" is intended to include both substituted and unsubstituted alkyl or loweralkyl unless otherwise indicated and these groups may be substituted with groups selected from halo (e.g., haloalkyl), alkyl, haloalkyl, alkenyl, alkynyl, cycloalkyl, cycloalkylalkyl, aryl, arylalkyl, heterocyclo, heterocycloalkyl, hydroxyl, alkoxy (thereby creating a polyalkoxy such as polyethylene glycol), alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-$S(O)_m$, haloalkyl-$S(O)_m$, alkenyl-$S(O)_m$, alkynyl-$S(O)_m$, cycloalkyl-$S(O)_m$, cycloalkylalkyl-$S(O)_m$, aryl-$S(O)_m$, arylalkyl-$S(O)_m$, heterocyclo-$S(O)_m$, heterocycloalkyl-$S(O)_m$, amino, carboxy, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1, 2 or 3.

"Alkenyl" as used herein alone or as part of another group, refers to a straight or branched chain hydrocarbon containing from 1 to 10 carbon atoms (or in loweralkenyl 1 to 4 carbon atoms) which include 1 to 4 double bonds in the normal chain.

Representative examples of alkenyl include, but are not limited to, vinyl, 2-propenyl, 3-butenyl, 2-butenyl, 4-pentenyl, 3-pentenyl, 2-hexenyl, 3-hexenyl, 2,4-heptadiene, and the like. The term "alkenyl" or "loweralkenyl" is intended to include both substituted and unsubstituted alkenyl or loweralkenyl unless otherwise indicated and these groups may be substituted with groups as described in connection with alkyl and loweralkyl above.

"Alkynyl" as used herein alone or as part of another group, refers to a straight or branched chain hydrocarbon containing from 1 to 10 carbon atoms (or in loweralkynyl 1 to 4 carbon atoms) which include 1 triple bond in the normal chain. Representative examples of alkynyl include, but are not limited to, 2-propynyl, 3-butynyl, 2-butynyl, 4-pentynyl, 3-pentynyl, and the like. The term "alkynyl" or "loweralkynyl" is intended to include both substituted and unsubstituted alkynyl or loweralkynyl unless otherwise indicated and these groups may be substituted with the same groups as set forth in connection with alkyl and loweralkyl above.

"Cycloalkyl" as used herein alone or as part of another group, refers to a saturated or partially unsaturated cyclic hydrocarbon group containing from 3, 4 or 5 to 6, 7 or 8 carbons (which carbons may be replaced in a heterocyclic group as discussed below). Representative examples of cycloalkyl include, cyclopropyl, cyclobutyl, cyclopentyl, cyclohexyl, cycloheptyl, and cyclooctyl. These rings may be optionally substituted with additional substituents as described herein such as halo or loweralkyl. The term "cycloalkyl" is generic and intended to include heterocyclic groups as discussed below unless specified otherwise.

"Heterocyclo" as used herein alone or as part of another group, refers to an aliphatic (e.g., fully or partially saturated heterocyclo) or aromatic (e.g., heteroaryl) monocyclic- or a bicyclic-ring system. Monocyclic ring systems are exemplified by any 5 or 6 membered ring containing 1, 2, 3, or 4 heteroatoms independently selected from oxygen, nitrogen and sulfur. The 5 membered ring has from 0-2 double bonds and the 6 membered ring has from 0-3 double bonds. Representative examples of monocyclic ring systems include, but are not limited to, azetidine, azepine, aziridine, diazepine, 1,3-dioxolane, dioxane, dithiane, furan, imidazole, imidazoline, imidazolidine, isothiazole, isothiazoline, isothiazolidine, isoxazole, isoxazoline, isoxazolidine, morpholine, oxadiazole, oxadiazoline, oxadiazolidine, oxazole, oxazoline, oxazolidine, piperazine, piperidine, pyran, pyrazine, pyrazole, pyrazoline, pyrazolidine, pyridine, pyrimidine, pyridazine, pyrrole, pyrroline, pyrrolidine, tetrahydrofuran, tetrahydrothiophene, tetrazine, tetrazole, thiadiazole, thiadiazoline, thiadiazolidine, thiazole, thiazoline, thiazolidine, thiophene, thiomorpholine, thiomorpholine sulfone, thiopyran, triazine, triazole, trithiane, and the like. Bicyclic ring systems are exemplified by any of the above monocyclic ring systems fused to an aryl group as defined herein, a cycloalkyl group as defined herein, or another monocyclic ring system as defined herein. Representative examples of bicyclic ring systems include but are not limited to, for example, benzimidazole, benzothiazole, benzothiadiazole, benzothiophene, benzoxadiazole, benzoxazole, benzofuran, benzopyran, benzothiopyran, benzodioxine, 1,3-benzodioxole, cinnoline, indazole, indole, indoline, indolizine, naphthyridine, isobenzofuran, isobenzothiophene, isoindole, isoindoline, isoquinoline, phthalazine, purine, pyranopyridine, quinoline, quinolizine, quinoxaline, quinazoline, tetrahydroisoquinoline, tetrahydroquinoline, thiopyranopyridine, and the like. These rings include quaternized derivatives thereof and may be optionally substituted with groups selected from halo, alkyl, haloalkyl, alkenyl, alkynyl, cycloalkyl, cycloalkylalkyl, aryl, arylalkyl, heterocyclo, heterocycloalkyl, hydroxyl, alkoxy, alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-S(O)$_m$, haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, amino, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1, 2 or 3.

"Aryl" as used herein alone or as part of another group, refers to a monocyclic carbocyclic ring system or a bicyclic carbocyclic fused ring system having one or more aromatic rings. Representative examples of aryl include, azulenyl, indanyl, indenyl, naphthyl, phenyl, tetrahydronaphthyl, and the like. In some embodiments aryl contains a "hetero" atom and is also a "heterocyclo" group as described above. The term "aryl" is intended to include both substituted and unsubstituted aryl unless otherwise indicated and these groups may be substituted with the same groups as set forth in connection with alkyl and loweralkyl above. More specifically, "aryl" groups as used herein may be substituted 1, 2, 3, or 4 or more times with independently selected halo (e.g., haloaryl), alkyl, haloalkyl, alkenyl, alkynyl, cycloalkyl, cycloalkylalkyl, aryl, arylalkyl, heterocyclo, heterocycloalkyl, hydroxyl, alkoxy (thereby creating a polyalkoxy such as polyethylene glycol), alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-S(O)$_m$, haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, amino, carboxy, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1, 2 or 3.

"Arylalkyl" as used herein alone or as part of another group, refers to an aryl group, as defined herein, appended to the parent molecular moiety through an alkyl group, as defined herein. Representative examples of arylalkyl include, but are not limited to, benzyl, 2-phenylethyl, 3-phenylpropyl, 2-naphth-2-ylethyl, and the like.

"Heteroaryl" as used herein is as described in connection with heterocyclo above.

"Alkoxy" as used herein alone or as part of another group, refers to an alkyl or loweralkyl group, as defined herein (and thus including substituted versions such as polyalkoxy), appended to the parent molecular moiety through an oxy group, —O—. Representative examples of alkoxy include, but are not limited to, methoxy, ethoxy, propoxy, 2-propoxy, butoxy, tert-butoxy, pentyloxy, hexyloxy and the like.

"Halo" as used herein refers to any suitable halogen, including —F, —Cl, —Br, and —I.

"Mercapto" as used herein refers to an —SH group.

"Azido" as used herein refers to an —N$_3$ group.

"Cyano" as used herein refers to a —CN group.

"Formyl" as used herein refers to a —C(O)H group.

"Carboxylic acid" as used herein refers to a —C(O)OH group.

"Hydroxyl" as used herein refers to an —OH group.

"Nitro" as used herein refers to an —NO$_2$ group.

"Acyl" as used herein alone or as part of another group refers to a —C(O)R radical, where R is any suitable substituent such as aryl, alkyl, alkenyl, alkynyl, cycloalkyl or other suitable substituent as described herein.

"Alkylthio" as used herein alone or as part of another group, refers to an alkyl group, as defined herein, appended to the parent molecular moiety through a thio moiety, as defined herein. Representative examples of alkylthio include, but are not limited, methylthio, ethylthio, tert-butylthio, hexylthio, and the like.

"Amino" as used herein means the radical —NH$_2$.

"Alkylamino" as used herein alone or as part of another group means the radical —NHR, where R is an alkyl group.

"Arylalkylamino" as used herein alone or as part of another group means the radical —NHR, where R is an arylalkyl group.

"Disubstituted-amino" as used herein alone or as part of another group means the radical —NR$_a$R$_b$, where R$_a$ and R$_b$ are independently selected from the groups alkyl, haloalkyl, alkenyl, alkynyl, cycloalkyl, cycloalkylalkyl, aryl, arylalkyl, heterocyclo, heterocycloalkyl.

"Acylamino" as used herein alone or as part of another group means the radical —NR$_a$R$_b$, where R$_a$ is an acyl group as defined herein and R$_b$ is selected from the groups hydrogen, alkyl, haloalkyl, alkenyl, alkynyl, cycloalkyl, cycloalkylalkyl, aryl, arylalkyl, heterocyclo, heterocycloalkyl.

"Acyloxy" as used herein alone or as part of another group means the radical —OR, where R is an acyl group as defined herein.

"Ester" as used herein alone or as part of another group refers to a —C(O)OR radical, where R is any suitable substituent such as alkyl, cycloalkyl, alkenyl, alkynyl or aryl.

"Amide" as used herein alone or as part of another group refers to a —C(O)NR$_a$R$_b$ radical, where R$_a$ and R$_b$ are any suitable substituent such as alkyl, cycloalkyl, alkenyl, alkynyl or aryl.

"Sulfoxyl" as used herein refers to a compound of the formula —S(O)R, where R is any suitable substituent such as alkyl, cycloalkyl, alkenyl, alkynyl or aryl.

"Sulfonyl" as used herein refers to a compound of the formula —S(O)(O)R, where R is any suitable substituent such as alkyl, cycloalkyl, alkenyl, alkynyl or aryl.

"Sulfonate" as used herein refers to a compound of the formula —S(O)(O)OR, where R is any suitable substituent such as alkyl, cycloalkyl, alkenyl, alkynyl or aryl.

"Sulfonic acid" as used herein refers to a compound of the formula —S(O)(O)OH.

"Sulfonamide" as used herein alone or as part of another group refers to a —S(O)$_2$NR$_a$R$_b$ radical, where R$_a$ and R$_b$ are any suitable substituent such as H, alkyl, cycloalkyl, alkenyl, alkynyl or aryl.

"Urea" as used herein alone or as part of another group refers to an —N(R$_c$)C(O)NR$_a$R$_b$ radical, where R$_a$, R$_b$ and R$_c$ are any suitable substituent such as H, alkyl, cycloalkyl, alkenyl, alkynyl or aryl.

"Alkoxyacylamino" as used herein alone or as part of another group refers to an —N(R$_a$)C(O)OR$_b$ radical, where R$_a$, R$_b$ are any suitable substituent such as H, alkyl, cycloalkyl, alkenyl, alkynyl or aryl.

"Aminoacyloxy" as used herein alone or as part of another group refers to an —OC(O)NR$_a$R$_b$ radical, where R$_a$ and R$_b$ are any suitable substituent such as H, alkyl, cycloalkyl, alkenyl, alkynyl or aryl.

Active compounds of the present invention may optionally be administered in conjunction with other compounds useful in iron chelation therapy (e.g., in the treatment of neurodegenerative diseases). The other compounds may optionally be administered concurrently. As used herein, the word "concurrently" means sufficiently close in time to produce a combined effect (that is, concurrently may be simultaneously, or it may be two or more events occurring within a short time period before or after each other).

The present invention is primarily concerned with the treatment of human subjects, but the invention may also be carried out on animal subjects, particularly mammalian subjects such as mice, rats, dogs, cats, livestock and horses for veterinary purposes, and for drug screening and drug development purposes.

1. Active Compounds.

Active compounds of the present invention include boronic ester-containing aroylhydrazone iron chelating agents in which the boronic ester conceals a latent phenolic oxygen that is a key donor of the hydrazone. Examples include compounds of Formula I (and in particular embodiments Formulas Ia-Ic):

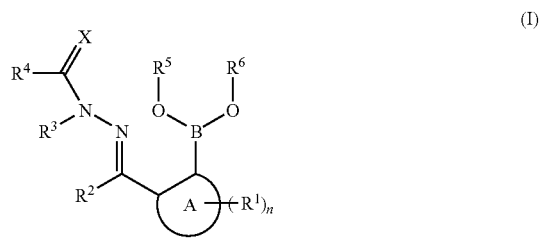

(I)

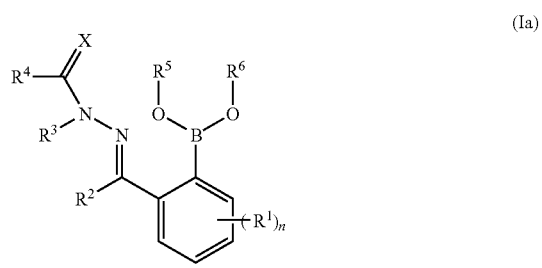

(Ia)

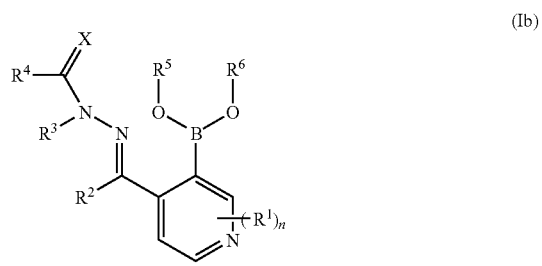

(Ib)

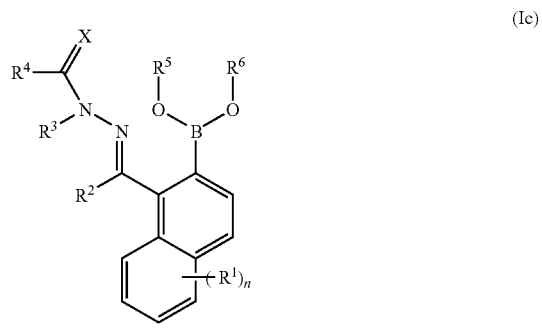

(Ic)

wherein:

X is O or S (preferably O);

A is aryl, non-limiting examples of which include monocyclic or fused ring aryl, optionally containing from 1 to 3 hetero atoms selected from N, O, and S (e.g., phenyl, pyridyl, naphthyl)(or stated otherwise, "A" represents an aromatic ring system such as benzene, pyridine, naphthalene, etc., which may be substituted or unsubstituted as described hereinabove and below);

n are each 0, 1, 2, 3, or 4 (or in some embodiments not more than 2 or 3 where fewer positions are available for substitution; it being understood that in the case of formula Ic groups $R^1$ may be substituted on either ring of the naphthyl group);

each $R^1$ is independently selected from the group consisting of: alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, arylalkyl, arylalkenyl, arylalkynyl, heteroaryl, heteroarylalkyl, heteroarylalkenyl, heteroarylalkynyl, alkoxy, halo, mercapto, azido, cyano, formyl, carboxylic acid, hydroxyl, nitro, acyl, aryloxy, alkylthio, amino, alkylamino, arylalkylamino, disubstituted amino, acylamino, acyloxy, ester, amide, sulfoxyl, sulfonyl, sulfonate, sulfonic acid, sulfonamide, urea, alkoxylacylamino, and aminoacyloxy (it being understood that $R^1$s may be on either ring in the fused ring system shown in Formula Ic);

$R^2$ and $R^3$ are each independently H, alkyl, or hydroxy;

$R^4$ is alkyl, cycloalkyl, heterocyclo, or aryl;

$R^5$ and $R^6$ are independently selected H, alkyl, haloalkyl, or together form an alkylene bridge (e.g., a C2 to C4, C6 or C8 alkylene bridge (e.g., —(CH$_2$)$_n$— where n is 2 to 4, 6 or 8), which may be unsubstituted or substituted from 1 to 4 times with alkyl, halo, or a fused aryl ring such as a fused phenyl);

and pharmaceutically acceptable salts or prodrugs thereof.

Specific examples of $R^5$ and $R^6$ include, but are not limited to, those where:

$R^5$ and $R^6$ are both H;

$R^5$ and $R^6$ are both CH$_3$;

or where $R^5$ and $R^6$ together form:

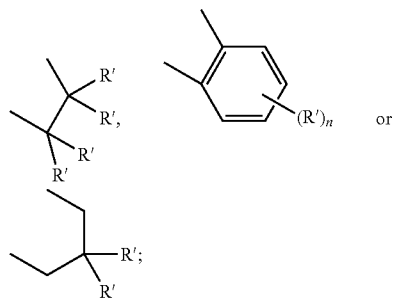

where n is 0, 1, 2, 3 or 4 and each R' is independently alkyl or halo.

Specific examples of compounds of the present invention include boronic-ester masked counterparts of compounds such as described in D. Kalinowski and D. Richardson, *Pharmacol. Rev.*, 57, 547 (2005)(see, e.g., FIG. 13 therein), examples of which include, but are not limited to:

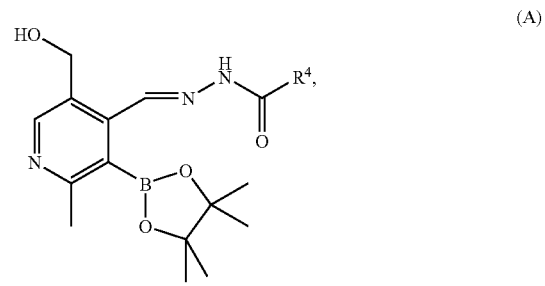
(A)

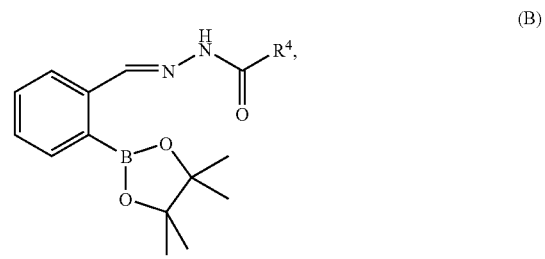
(B)

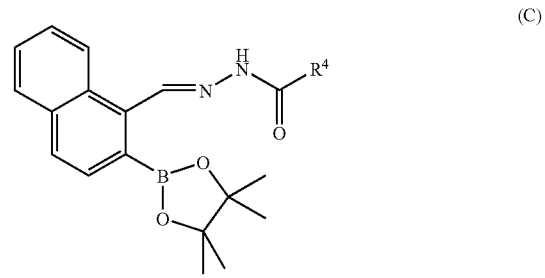
(C)

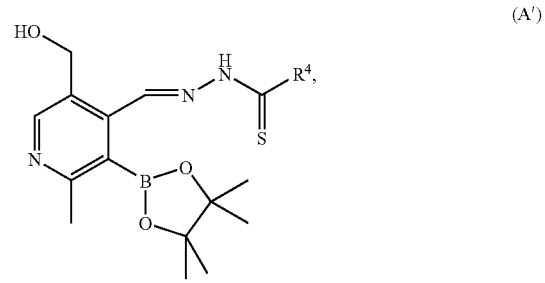
(A')

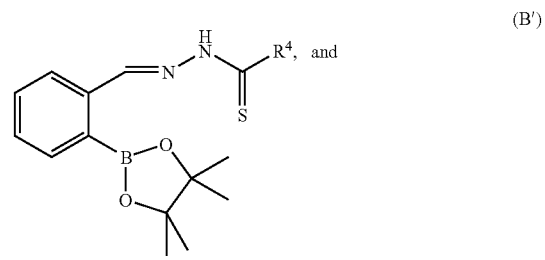
(B')

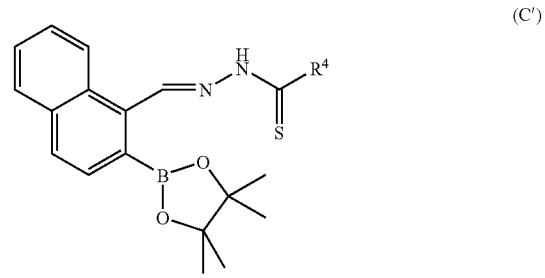
(C')

where $R^4$ is as described generally in connection with Formula I above, or more specifically may be as in Table A below:

TABLE A

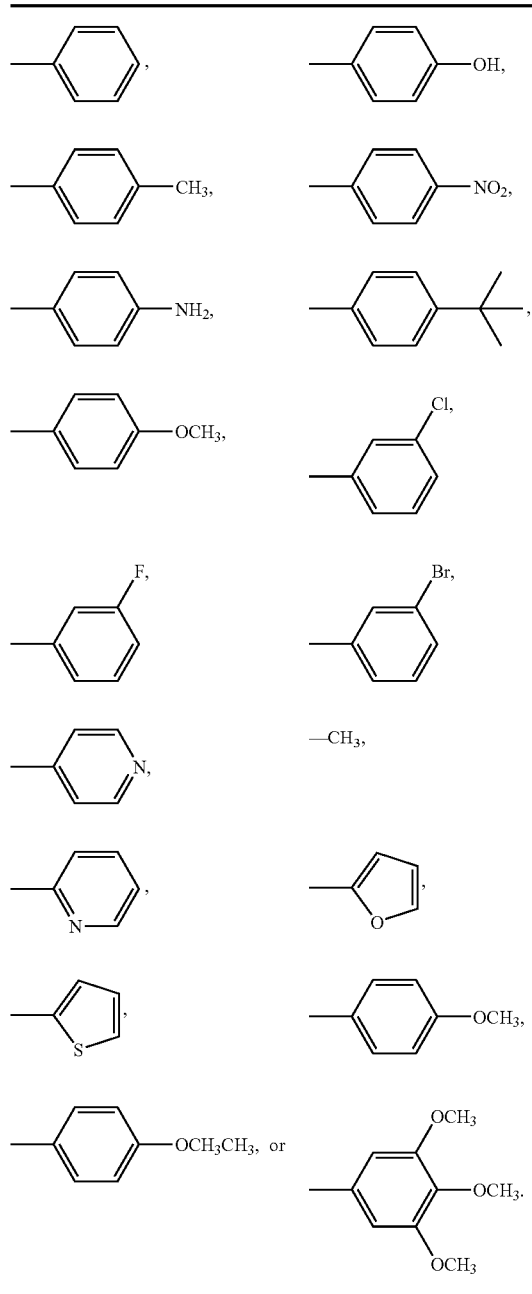

Still other examples of compounds of the present invention include, but are not limited to:

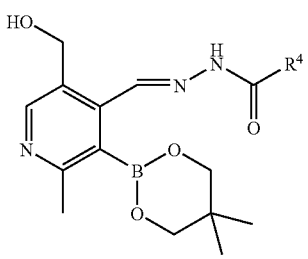

(E)

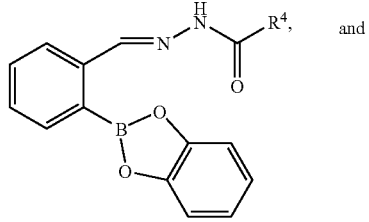

(F)

and

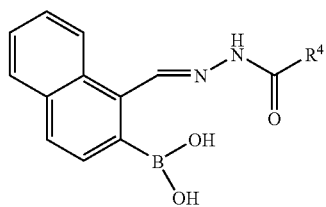

(G)

where $R^4$ is as described generally in connection with Formula I above, or more specifically may be as in Table A above.

Compounds of the present invention can be made in accordance with known techniques or variations thereof that will be apparent to those skilled in the art given known techniques and the present disclosure. See U.S. Pat. Nos. 6,989,397 and 6,329,378; see also D. Richardson and P. Ponka, *J Lab Clin Med.* 131, 306-314 (1998); T. Simunek et al., *J. Mol. Cell. Cardiol.* 39, 345-354 (2005); D. Kalinowski and D. Richardson, *Pharmacol. Rev.* 57, 547-583 (2005); M. Yang et al., *J. Am. Chem. Soc.* 126, 15392-15393 (2004); E. Miller et al., *J. Am. Chem. Soc* 127, 16652-16659 (2005).

The active compounds disclosed herein can, as noted above, be prepared in the form of their pharmaceutically acceptable salts. Pharmaceutically acceptable salts are salts that retain the desired biological activity of the parent compound and do not impart undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; (b) salts formed from elemental anions such as chlorine, bromine, and iodine, and (c) salts derived from bases, such as ammonium salts, alkali metal salts such as those of sodium and potassium, alkaline earth metal salts such as those of calcium and magnesium, and salts with organic bases such as dicyclohexylamine and N-methyl-D-glucamine.

Pharmaceutically acceptable prodrugs as used herein refers to those prodrugs of the active compounds of the present invention which are, within the scope of sound medical judgment, suitable for use in contact with the tissues of humans and lower animals without undue toxicity, irritation, allergic response and the like, commensurate with a reasonable risk/benefit ratio, and effective for their intended use, as well as the zwitterionic forms, where possible, of the compounds of the invention. The term "prodrug" refers to compounds that are rapidly transformed in vivo to yield the parent compound of the above formulae, for example, by hydrolysis in blood. A thorough discussion is provided in T. Higuchi and V. Stella, Prodrugs as Novel delivery Systems, Vol. 14 of the A.C.S. Symposium Series and in Edward B. Roche, ed., Bioreversible Carriers in Drug Design, American Pharmaceutical Association and Pergamon Press, 1987, both of which are incorporated by reference herein. See also U.S. Pat. No. 6,680,299 Examples include a prodrug that is metabolized in vivo by a subject to an active drug having an activity of active compounds as described herein, wherein the prodrug is an ester of an alcohol or carboxylic acid group, if such a group is present in the compound; an acetal or ketal of an alcohol group, if such a group is present in the compound; an N-Mannich base or an imine of an amine group, if such a group is present in the compound; or a Schiff base, oxime, acetal, enol ester, oxazolidine, or thiazolidine of a carbonyl group, if such a group is present in the compound, such as described in U.S. Pat. No. 6,680,324 and U.S. Pat. No. 6,680,322.

2. Pharmaceutical Formulations.

The active compounds described above may be formulated for administration in a pharmaceutical carrier in accordance with known techniques. See, e.g., Remington, *The Science And Practice of Pharmacy* (9$^{th}$ Ed. 1995). In the manufacture of a pharmaceutical formulation according to the invention, the active compound (including the physiologically acceptable salts thereof) is typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.01 or 0.5% to 95% or 99% by weight of the active compound. One or more active compounds may be incorporated in the formulations of the invention, which may be prepared by any of the well known techniques of pharmacy comprising admixing the components, optionally including one or more accessory ingredients.

The formulations of the invention include those suitable for oral, rectal, topical, buccal (e.g., sub-lingual), vaginal, parenteral (e.g., subcutaneous, intramuscular, intradermal, or intravenous), topical (i.e., both skin and mucosal surfaces, including airway surfaces) and transdermal administration, although the most suitable route in any given case will depend on the nature and severity of the condition being treated and on the nature of the particular active compound which is being used.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Formulations suitable for buccal (sub-lingual) administration include lozenges comprising the active compound in a flavoured base, usually sucrose and acacia or tragacanth; and pastilles comprising the compound in an inert base such as gelatin and glycerin or sucrose and acacia.

Formulations of the present invention suitable for parenteral administration comprise sterile aqueous and non-aqueous injection solutions of the active compound, which preparations are preferably isotonic with the blood of the intended recipient. These preparations may contain anti-oxidants, buffers, bacteriostats and solutes which render the formulation isotonic with the blood of the intended recipient. Aqueous and non-aqueous sterile suspensions may include suspending agents and thickening agents. The formulations may be presented in unit\dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described. For example, in one aspect of the present invention, there is provided an injectable, stable, sterile composition comprising a compound of Formula (I), or a salt thereof, in a unit dosage form in a sealed container. The compound or salt is provided in the form of a lyophilizate which is capable of being reconstituted with a suitable pharmaceutically acceptable carrier to form a liquid composition suitable for injection thereof into a subject. The unit dosage form typically comprises from about 10 mg to about 10 grams of the compound or salt. When the compound or salt is substantially water-insoluble, a sufficient amount of emulsifying agent which is physiologically acceptable may be employed in sufficient quantity to emulsify the compound or salt in an aqueous carrier. One such useful emulsifying agent is phosphatidyl choline.

Formulations suitable for rectal administration are preferably presented as unit dose suppositories. These may be prepared by admixing the active compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3 (6):318 (1986)) and typically take the form of an optionally buffered aqueous solution of the active compound. Suitable formulations comprise citrate or bis\tris buffer (pH 6) or ethanol/water and contain from 0.1 to 0.2M active ingredient.

Further, the present invention provides liposomal formulations of the compounds disclosed herein and salts thereof. The technology for forming liposomal suspensions is well known in the art. When the compound or salt thereof is an aqueous-soluble salt, using conventional liposome technology, the same may be incorporated into lipid vesicles. In such an instance, due to the water solubility of the compound or salt, the compound or salt will be substantially entrained within the hydrophilic center or core of the liposomes. The lipid layer employed may be of any conventional composition and may either contain cholesterol or may be cholesterol-free. When the compound or salt of interest is water-insoluble, again employing conventional liposome formation technology, the salt may be substantially entrained within the hydrophobic lipid bilayer which forms the structure of the liposome. In either instance, the liposomes which are produced may be reduced in size, as through the use of standard sonication and homogenization techniques.

Of course, the liposomal formulations containing the compounds disclosed herein or salts thereof, may be lyophilized to produce a lyophilizate which may be reconstituted with a pharmaceutically acceptable carrier, such as water, to regenerate a liposomal suspension.

Other pharmaceutical compositions may be prepared from the water-insoluble compounds disclosed herein, or salts thereof, such as aqueous base emulsions. In such an instance, the composition will contain a sufficient amount of pharmaceutically acceptable emulsifying agent to emulsify the desired amount of the compound or salt thereof. Particularly useful emulsifying agents include phosphatidyl cholines, and lecithin.

In addition to compounds of formula (I) or their salts, the pharmaceutical compositions may contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multidose use. Of course, as indicated, the pharmaceutical compositions of the present invention may be lyophilized using techniques well known in the art.

3. Dosage and Routes of Administration.

As noted above, the present invention provides pharmaceutical formulations comprising the active compounds (including the pharmaceutically acceptable salts thereof), in pharmaceutically acceptable carriers for oral, rectal, topical, buccal, parenteral, intramuscular, intradermal, or intravenous, and transdermal administration.

The therapeutically effective dosage of any one active agent, the use of which is in the scope of present invention, will vary somewhat from compound to compound, and patient to patient, and will depend upon factors such as the age and condition of the patient and the route of delivery. Such dosages can be determined in accordance with routine pharmacological procedures known to those skilled in the art. As a general proposition, a dosage from about 0.1 or 1.0 to about 250 or 500 mg/kg will have therapeutic efficacy, with all weights being calculated based upon the weight of the active compound, including the cases where a salt is employed. Toxicity concerns at the higher level may restrict intravenous dosages to a lower level such as up to about 10 mg/kg, with all weights being calculated based upon the weight of the active base, including the cases where a salt is employed. A dosage from about 10 mg/kg to about 200 mg/kg may be employed for oral administration. Typically, a dosage from about 1 mg/kg to 100 mg/kg may be employed for intramuscular injection. The duration of the treatment is usually once per day for a period of two to three weeks or until the condition is essentially controlled. Lower doses given less frequently can be used prophylactically to prevent or reduce the incidence of recurrence of the disease.

4. Combination Treatments.

In another embodiment, it is envisioned to use an active compound of the invention in combination with other therapeutic modalities, in like manner as described in U.S. Pat. No. 6,946,441 to Long et al. Thus, in addition to the therapies described above, one may also provide to the patient more additional therapies for the treatment of neurodegenerative disease. The particular therapy will depend upon the disease being treated. Examples of such therapies for Parkinson's disease include but are not limited to levodopa (L-DOPA; with or without carbidopa), dopamine agonists (such as apomorphine, bromocriptine, pergolide, pramipexole, ropinirole, etc.) anticholinergics such as atropine, scopolamine, glycopyrrolate, trihexyphenidyl, benztropine mesylate, procyclidine, etc.), monoamine oxidase (MAO-B) inhibitors such as selegiline, COMT inhibitors (preferably taken with levodopa) such as entacapone and tolcapone and other medications such as amantadine, etc., and including pharmaceutically acceptable salts and prodrugs thereof, and combinations of any of the foregoing. See, e.g., U.S. Pat. No. 6,833,478.

The additional active agent may be administered separately from the active agents of the present invention, or the two combined together in a single composition.

Compositions containing an active agent of the invention in combination with an additional active or therapeutic agent such as an antiparkinson's agent are prepared in like manner as described above and techniques that will be apparent to those skilled in the art. Such compositions may be prepared in any suitable unit dosage form including injectable forms and oral dosage forms such as tablets and capsules, as described above.

The present invention is explained in greater detail in the following non-limiting Examples.

Example 1

Herein we present our pro-chelator, BSIH, in which a boronic ester conceals a latent phenolic oxygen that is a key donor atom of salicylaldehyde isonicotinoyl hydrazone (SIH), a member of the well known aroylhydrazone class of chelators that have shown considerable promise as orally available agents (Kalinowski, D. S.; Richardson, D. R., *Pharmacol. Rev.* 2005, 57, 547-583; Horackova, M. et al., *Cardiovasc. Res.* 2000, 47, 529-536; Simunek, T. et al., *J. Mol. Cell. Cardiol.* 2005, 39, 345-354.).

Aryl boronic esters react selectively with $H_2O_2$ to produce phenols, which are excellent iron-binding groups that are often incorporated into multi-dentate iron ligands. Boronate-based fluoresceins have been used as intracellular fluorescence probes of $H_2O_2$, work that demonstrates the selectivity and biocompatibility of this class of molecules (Chang, M. C. Y. et al., *J. Am. Chem. Soc.* 2004, 126, 15392-15393; Miller, E. W. et al., *J. Am. Chem. Soc.* 2005, 127, 16652-16659).

The pro-chelate BSIH is readily obtained by condensation of isonicotinic acid hydrazide with (2-formylphenyl)boronic acid pinacol ester (Bsal). The X-ray structure (data not shown) reveals an E configuration about the C7=N3 double bond and an anti configuration of the B atom with respect to the imine N3 atom. NMR reveals that other conformations are accessible in solution (see Supp Info). Upon conversion to SIH, the OH group adopts a syn conformation that is favorably disposed for tridentate metal chelation via the carbonyl O, the imine N, and the deprotonated phenolate O⁻ (Yin, H. D. et al., *J. Organomet. Chem.* 2005, 690, 3714-3719).

BSIH does not form a complex with $Fe^{3+}$, as shown in FIG. 1 by the absence of new features in the UV-vis spectrum of a solution containing BSIH and $Fe(NO_3)_3$. Addition of $H_2O_2$ to this mixture, however, results in formation of a new spectrum matching that of $[Fe(SIH)_2]^+$, or $[Fe(SIH)]^{2+}$ at low ligand/metal ratios. These two species are distinguishable by a ligand-field band centered at 658 nm that is more pronounced in the mono species compared to the bis species (FIG. 1 inset).

FIG. 2 shows the time course for iron complex formation following addition of excess $H_2O_2$ to a methanol solution of $Fe(NO_3)_3$ and BSIH. Although the kinetics are complicated by the mono to bis $Fe(SIH)_x$ coordination, the data fit a pseudo first-order expression to give $k_{obs}=1.6\times10^{-3}$ s$^{-1}$. This value is consistent with preliminary kinetic data for the conversion of BSIH to SIH in the absence of iron (not shown), indicating that the rate-limiting step for iron sequestration is oxidation of BSIH to SIH, followed by rapid metal complexation.

In order to test the effectiveness of BSIH for inhibiting OH. formation, we used an in vitro deoxyribose assay in which hydroxyl radicals that are generated via typical Fenton conditions of $Fe^{3+}$, ascorbic acid, and $H_2O_2$, degrade deoxyribose to give products that form a chromophore with thiobarbituric acid (TBA) with $\lambda_{max}$ at 532 nm (Halliwell, B. et al., *Anal. Biochem.* 1987, 165, 215-219). FIG. 3 displays the effect of increasing chelator concentration on the degradation of deoxyribose under these conditions. Values of $A/A_o$ above 1 indicate that the additive promotes OH. formation, whereas values below 1 indicate that the additive either scavenges OH. more efficiently than deoxyribose, or that it inhibits iron-catalyzed OH. formation via effective iron chelation. EDTA, a ligand known to promote Fenton chemistry, causes a significant increase in $A/A_o$ (data not shown), whereas desferrioxamine (DFO) and SIH, chelators known to inhibit Fenton chemistry (Hermes-Lima, M. et al., *Biochim. Biophys. Acta* 2000, 1523, 154-160), show a decrease in $A/A_o$. As shown in FIG. 4, BSIH protects against deoxyribose degradation as well as both DFO and SIH.

In order to show that the protective effect of BSIH is not solely due to consumption of $H_2O_2$, we tested the boronate-masked salicylaldehyde, Bsal, which converts to salicylaldehyde (Sal) in the presence of $H_2O_2$. Neither Bsal nor Sal has a significant influence on the deoxyribose assay, as shown by the nearly constant $A/A_o$ values near unity in FIG. 3. Taken together, these data indicate that the protective effect of BSIH against deoxyribose degradation derives from its $H_2O_2$-dependent conversion to SIH, which in turn provides the right coordination environment around Fe to prevent iron-promoted OH. generation.

Experimental

Materials and Instrumentation. Chemicals were obtained from Fisher Scientific or Acros Organics and used without further purification unless otherwise noted; (2-formylphenyl) boronic acid pinacol ester was purchased from Combi-Blocks, Inc. All solvents were reagent grade and all aqueous solutions were prepared from nanopure water. Solutions of $FeCl_3$ (1 mM in 10 mM HCl) and ascorbic acid (100 mM) were prepared fresh daily. Stock solutions of thiobarbituric acid (TBA; 1% w/v in 0.05 M NaOH), trichloroacetic acid (TCA; 2.8% w/v), 2-deoxyribose (300 mM), $H_2O_2$ (10 mM) were prepared weekly. SIH, BSIH, EDTA, salicylaldehyde, formyl phenyl boronic acid and desferrioxamine (DFO) stock solutions (1 mM) were prepared weekly in 20 mM HEPES buffer (N-(2-hydroxyethyl)-piperazine-N'-2-ethanesulfonic acid), pH 7.4. UV-vis spectra were recorded on a Phototonics Model 420 Fiber Optic CCD Array UV-vis spectrophotometer. $^1H$ and $^{13}C$ NMR spectra were recorded on a Varian Inova 400 spectrometer. IR Spectra were recorded on a Nicolet 360 FT-IR. Ionization mass spectrometry (ESI-MS) was preformed on an Agilent 1100 Series LC/MSD trap spectrometer with a Daly conversion dynode detector. Samples were infused via a Harvard apparatus syringe pump at 33 μL/min. Ionization was achieved in the positive- or negative-ion mode by application of +5 or −5 kV at the entrance to the capillary; the pressure of the nebulizer gas was 20 psi. The drying gas was heated to 325° C. at a flow of 7 L/min. Full-scan mass spectra were recorded in the mass/charge (m/z) range of 100-2000.

2-Deoxyribose Assay. The formation of hydroxyl radicals was measured by using a 2-deoxyribose oxidative degradation assay (Aruoma, O. I., Deoxyribose Assay for Detecting Hydroxyl Radicals. *In Methods in Enzymol.,* 1994; Vol. 233, pp 57-66; Halliwell, B. et al., *Anal. Biochem.* 1987, 165, 215-219). In this assay, hydroxyl radicals, generated by reaction of an iron complex with $H_2O_2$ in the presence of ascorbic acid as a reducing agent, attack 2-deoxyribose to form malondialdehyde, which upon heating with TBA at low pH yields a pink chromogen ($\lambda_{max}$=532 nm). Scavengers that react more effectively with hydroxyl radicals than deoxyribose result in less chromogen formation. Chelators that prevent iron from reacting with $H_2O_2$ also result in a decrease in absorption at 532 nm. Many standard buffers such as HEPES and TRIS are hydroxyl radical scavengers; therefore, we performed all assays in 50 mM $NaH_2PO_4$ buffered to pH 7.4. Our standard reaction conditions consisted of 1-mL buffered solutions prepared by sequential addition of the following reagents at their final concentrations: chelator (0-400 μM), $FeCl_3$ (10 μM), 2-deoxyribose (15 mM), $H_2O_2$ (200 μM) and ascorbic acid (2 mM). The reactions were stirred for 60 min at 37° C., then quenched with 1 mL of TBA (1% w/v in 0.05 M NaOH) and 1 mL of TCA (2.8% w/v in water). After heating to 100° C. for 20 min, the solutions were cooled to room temperature and their absorbance at 532 nm recorded. The data are reported as $A/A_o$, where A is the absorbance at a 532 nm at a specific chelator concentration, and $A_o$ is the absorbance at 532 nm for the background reaction containing no added chelator. All measurements were done in triplicate, and error bars reflect the standard deviation from triplicate runs.

Preparation salicylaldehyde isonicotinoyl hydrazone (SIH). SIH was prepared by a Schiff base condensation procedure similar to that described previously (Edward, J. T. et al., *J. Chem. Eng. Data* 1988, 33, 538-540; Ponka, P. et al., *Febs Lett.* 1979, 97, 317-321). Equimolar quantities of nearly saturated solutions of isonicotinic acid hydrazide (1 mmol, 0.137 g) and salicylaldehyde (1 mmol, 0.122 g), both in 0.1 M pH 4.5 sodium acetate buffer were added to a 25-mL round-bottom flask equipped with a stir bar. The reaction mixture was stirred over an oil bath at 100° C. for 4 min. The white insoluble product was collected via vacuum filtration and washed with water. Slow evaporation from ethanol afforded white needle-like crystals in 98% yield. $^1$H NMR (DMSO): δ 6.93 (2H, m), 7.319 (1H, td, J=1.68, J=6.69), 7.605 (1H, dd, J=1.49, J=7.67), 7.847 (2H, dd, J=1.65, J=4.4), 8.683 (1H, s), 8.801 (2H, dd, J=1.59, J=4.4), 11.017 (1H, s), 12.288 (1H, s). $^{13}$C NMR (DMSO): δ 116.4, 119.5, 121.5, 129.2, 131.7, 134.0, 148.9, 150.4, 157.5; MS (ESI): m/z 242.1 (M+H$^+$), 264.1 (M+Na$^+$), 240.1 (M−H$^+$); IR (neat, cm$^{-1}$): 3176, 2999, 2840, 1676, 1612. 1562, 1469, 1402, 1273, 1155, 761, 679; UV-vis (MeOH) mm (M$^{-1}$ cm$^{-1}$): 214 (19,260), 286 (14,800), 332 (13,140).

Preparation of Isonicotinic acid [2-(4,4,5,5-tetramethyl-[1,3,2]dioxaborolan-2-yl)-benzylidene]-hydrazide (BSIH). A portion of (2-formylphenyl)boronic acid pinacol ester (1 mmol, 0.232 g) was added to a nearly saturated solution of isonicotinic acid hydrazide (1 mmol, 0.137 g) in 0.1 M pH 4.5 sodium acetate buffer. The reaction mixture was stirred over an oil bath at 100° C. in for 4 min. The white insoluble product was collected via vacuum filtration, washed with water, and dried in vacuo to give an off-white powder in 67% yield. Recrystallization by slow evaporation of CH$_2$Cl$_2$ or vapor diffusion of CH$_2$Cl$_2$ and hexanes afforded translucent plates suitable for X-ray diffraction. $^1$H NMR (DMSO): δ 1.341 (12H, s), 7.447 (2H, td, J=1.20, J=6.47), 7.565 (1H, t, J=7.07), 7.736 (1H, d, J=6.72), 7.818 (2H, dd, J=1.47, J=4.49), 8.029 (1H, d, J=7.68), 8.791 (2H, d, J=5.8), 8.963 (1H, s), 12.20 (1H, s); $^{13}$C NMR (DMSO): δ 62.07, 121.45, 138.27, 159.21, 163.11, 166.70, 168.59, 173.04, 176.79, 186.85, 187.74, 187.89; MS (ESI): m/z 352.3 (M+H$^+$), 374.3 (M+Na$^+$), 350.1 (M−H$^+$); IR (neat, cm$^{-1}$): 3179, 3059, 2974, 1643, 1550, 1479, 1346, 1292, 1141. 1056; UV-vis (MeOH) nm (M$^{-1}$ cm$^{-1}$): 208 (20,320), 302 (19,530).

Preparation of [Fe(SIH)(CH$_3$OH)Cl$_2$]. [Fe(SIH)(CH$_3$OH)Cl$_2$] was prepared by following a procedure described for related compounds (Richardson, D. R.; Bernhardt, P. V. *J. Biol. Inorg. Chem.* 1999, 4, 266-273; Aruffo, A. A. et al., *Acta Crystallogr. Sec. C* 1984, 40, 1164-1169). A portion FeCl$_3$.6H$_2$O (0.63 mmol, 0.170 g) was added to a solution of SIH (0.5 mmol, 0.120 g) and Et$_3$N (0.5 mmol, 0.070 mL) in 13 mL of MeOH in a round-bottom flask. The reaction mixture was refluxed gently for 1 h. Upon cooling, the insoluble product was collected via vacuum filtration and washed with MeOH, H$_2$O and acetone. Slow evaporation from MeOH afforded a dark red powder in 40% yield. MS (ESI): m/z 364.9 (M−H$^+$); IR (neat, cm$^{-1}$): 3054, 1972, 1587, 1502, 1431, 1347, 1205, 1347, 1147, 809. 739; UV-vis (MeOH) nm$^1$ cm$^{-1}$): 294 (17,140), 348 (11,970), 658 (440).

Preparation of [Fe(SIH)$_2$](NO$_3$). [Fe(SIH)$_2$]+ was prepared by following a procedure described for related compounds (Richardson, D. R.; Bernhardt, P. V., supra). A portion of Fe(NO$_3$)$_3$.9H$_2$O in 30 mL of MeOH was added dropwise to a refluxing solution of SIH (1.72 mmol, 0.5 g) in 125 mL of MeOH. After refluxing for 1 hour, the solution was cooled and the black precipitate was collected by vacuum filtration and washed with EtOH and Et$_2$O. Slow diffusion of Et$_2$O into DMSO afforded a black powder in 57% yield. MS (ESI): m/z 534.2 (M−H$^+$), 536.3 (M+H$^+$). IR (neat, cm$^{-1}$): 3344, 1598, 1534, 1501; UV-vis (MeOH) nm (M$^{-1}$ cm$^{-1}$): 294 (16,830), 332 (12,930).

X-ray Data Collection and Structure Solution Refinement. Translucent plates of BSIH were grown by slow evaporation of CH$_2$Cl$_2$. The crystal was mounted on the tip of a glass fiber and held in place by epoxy glue. Data were collected at 298 K on a Bruker Kappa Apex II CCD diffractometer equipped with a graphite monochromator and a Mo Kα fine-focus sealed tube (λ=0.71073 Å) operated at 1.75 kW power (50 kV, 35 mA). The detector was placed at a distance of 5.010 cm from the crystal. A total of 1548 frames were collected with a scan width of 0.5° in and an exposure time of 120.0 sec/frame. The frames were integrated with the Bruker SAINT v7.12A software package using a narrow-frame integration algorithm. Empirical absorption corrections were applied using SADABS v2.10 and the structure was checked for higher symmetry with PLATON v1.07. The structure was solved by direct methods with refinement by full-matrix least-squares based on F$^2$ using the Bruker SHELXTL Software Package. All non-hydrogen atoms were refined anisotropically. Hydrogen atoms of sp$^2$ hybridized carbons and nitrogens were located directly from the difference Fourier maps; all others were calculated (data not shown).

The foregoing is illustrative of the present invention, and is not to be construed as limiting thereof. The invention is defined by the following claims, with equivalents of the claims to be included therein.

What is claimed is:
1. A compound of Formula I:

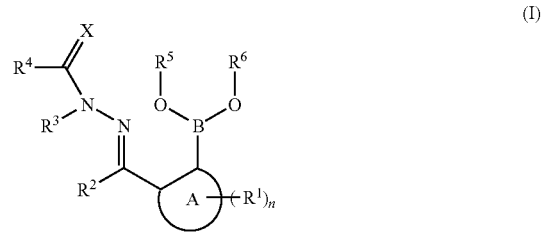

wherein:
X is O or S;
A is aryl;
n is an integer from 1 to 4;
each R$^1$ is independently selected from the group consisting of: alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, arylalkyl, arylalkenyl, arylalkynyl, heteroaryl, heteroarylalkyl, heteroarylalkenyl, heteroarylalkynyl, alkoxy, halo, mercapto, azido, cyano, formyl, carboxylic acid, hydroxyl, nitro, acyl, aryloxy, alkylthio, amino, alkylamino, arylalkylamino, disubstituted amino, acylamino, acyloxy, ester, amide, sulfoxyl, sulfonyl, sulfonate, sulfonic acid, sulfonamide, urea, alkoxylacylamino, and aminoacyloxy;
R$^2$ and R$^3$ are each independently H, alkyl, or hydroxy;
R$^4$ is alkyl, cycloalkyl, heterocyclo, or aryl;
R$^5$ and R$^6$ are independently selected H, alkyl, or haloalkyl, or together form an alkylene bridge, which alkylene bridge may be unsubstituted or substituted from 1 to 4 times with alkyl, halo, or a fused aryl ring; and pharmaceutically acceptable salts thereof.

2. The compound of claim 1, wherein X is O.

3. The compound of claim 1, wherein said compound has a structure of Formula Ia:

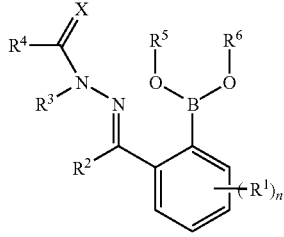

(Ia)

wherein n, $R^1$, $R^2$, $R^3$, $R^4$, $R^5$ and $R^6$ are as given in claim 1;

and the pharmaceutically acceptable salts thereof.

4. The compound of claim 1, wherein said compound has a structure of Formula Ib:

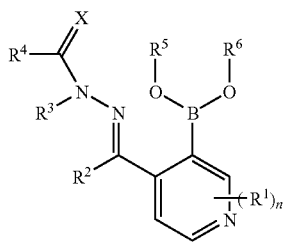

(Ib)

wherein n, $R^1$, $R^2$, $R^3$, $R^4$, $R^5$ and $R^6$ are as given in claim 1;

and the pharmaceutically acceptable salts thereof.

5. The compound of claim 1, wherein said compound has a structure of Formula Ic:

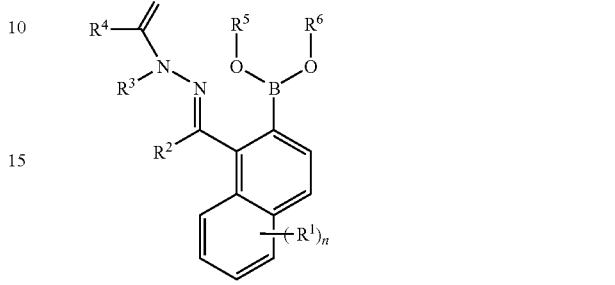

(Ic)

wherein n, $R^1$, $R^2$, $R^3$, $R^4$, $R^5$ and $R^6$ are as given in claim 1;

and the pharmaceutically acceptable salts thereof.

6. A pharmaceutical formulation comprising a compound of claim 1 in a pharmaceutically acceptable carrier.

7. The pharmaceutical formulation of claim 6 in oral dose form.

8. The pharmaceutical formulation of claim 7, wherein said oral dose form is a tablet or capsule.

9. A method of iron chelation therapy in a subject in need thereof, comprising administering said subject a therapeutically effective amount of a compound of claim 1.

\* \* \* \* \*